United States Patent [19]

Jaffe et al.

[11] Patent Number: 4,724,265

[45] Date of Patent: Feb. 9, 1988

[54] PROCESS FOR PREPARING LIQUID TRIARYL THIOPHOSPHATE MIXTURES

[75] Inventors: Fred Jaffe, Ossining; Alan M. Aaronson, Fresh Meadows, both of N.Y.

[73] Assignee: Stauffer Chemical Company, Westport, Conn.

[21] Appl. No.: 863,656

[22] Filed: May 15, 1986

[51] Int. Cl.$^4$ .............................................. C07F 9/165
[52] U.S. Cl. ...................................... 558/123; 558/92; 558/211; 252/609
[58] Field of Search ....................... 558/123, 211, 92; 252/609

[56] References Cited

U.S. PATENT DOCUMENTS

| | | | |
|---|---|---|---|
| 2,250,049 | 7/1941 | Moyle | 558/123 |
| 3,829,565 | 8/1974 | Kishino et al. | 558/123 |
| 3,839,510 | 10/1974 | Kudamatsu et al. | 558/123 |

*Primary Examiner*—Anton H. Sutto
*Attorney, Agent, or Firm*—Paul J. Juettner

[57] ABSTRACT

Liquid mixed triaryl thiophosphate mixtures can be prepared by forming a mixture of phenol and substituted phenols, forming a phosphite from that mixture and sulfurizing the phosphite, washing the thiophosphate with aqueous base, and drying the so washed thiophosphate under mild conditions. The products are liquid while containing at least 25 percent symmetrical triaryl thiophosphate. Colorless and odorless products are prepared.

16 Claims, No Drawings

PROCESS FOR PREPARING LIQUID TRIARYL THIOPHOSPHATE MIXTURES

The present invention relates to an improved process for preparing liquid mixed triaryl thiophosphate flame retardants for synthetic polymers.

BACKGROUND OF THE INVENTION

Triaryl thiophosphates are known plasticizing and flame retardant agents for polymers. However, symmetrical triaryl thiophosphates, e.g., triphenyl phosphate, are crystalline solids. This detracts from their use as plasticizers as they have a tendency to crystallize and bloom to the surface of the plasticized composition. As solids, these compounds are difficult to process and handle. They also have a disagreeable $H_2S$ odor.

Mixed triaryl thiophosphates, such as di-phenyl mono-p-tertiarybutylphenyl thiophosphate, as disclosed in U.S. Pat. No. 2,250,049 are liquid. These mixed triaryl thiophosphates are useful as plasticizing agents and fire retardants for polymers. However, these agents are not substantially odor free.

The mixed triaryl thiophosphates as disclosed in U.S. Pat. No. 2,250,049 are prepared by reacting a phosphorus trihalide with two molecular equivalents of phenol and thereafter reacting the intermediate product with one molecular equivalent of a phenol having nine or more carbon atoms. The reverse sequence is also disclosed as operative. The reaction product consists mainly of the desired mixed triaryl phosphite but may contain minor amounts of other mixed triaryl phosphites as well as symmetrical triaryl phosphites. The thiophosphate is then formed by reaction of the phosphite with sulfur. The product can be used directly or vacuum distilled. The sulfurization step can be eliminated by the use of thiophosphoryl chloride.

In the preparation of these materials, fractional distillation is used to purify the product. However, distillation results in decomposition of the product resulting in the formation of disagreeable odors. It would be desirable to prepare purified liquid triaryl thiophosphates without the need for distillation and the resulting odor problem.

It is well known that the percent phosphorus added as part of a flame retardant is correlatable to the effectiveness of the flame retardant. Also, the expense of an additive can be reflected in the number and complexity of processing steps needed to prepare the additive as well as the amount which must be added to achieve a certain degree of effectiveness.

SUMMARY OF THE INVENTION

In accordance with the present invention, it has been found that a stable and odorless liquid triaryl thiophosphate can be prepared using fewer and less complicated processing steps as well as increasing the percentage of phosphorus in the flame retardant. An odorless thiophosphate composition which is liquid at room temperature is provided comprising at least 25% solid symmetrical triaryl thiophosphate in combination with a liquid substituted triaryl thiophosphate in an amount at least sufficient to form a liquid thiophosphate composition at room temperature when combined with said solid triaryl thiophosphate. The composition of the invention requires only a portion of substituted triaryl thiophosphate to provide a liquid flame retardant, thereby maintaining higher molecular weight species to a minimum resulting in an increase in the amount of phosphorus per unit weight of the composition.

These thiophosphate mixtures can be prepared in situ utilizing a reaction method which reduces the number of process steps from those known in the art. The process for preparing mixed aryl thiophosphates is concluded with a final alkaline wash and a mild drying step to provide a substantially superior odorless product which requires less substitution than taught by the prior art.

DETAILED DESCRIPTION OF THE INVENTION

The compositions prepared in accordance with the present invention are mixtures of triaryl thiophosphates of the formula:

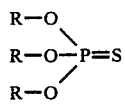

wherein R represents the same or different aryl radicals of up to 2 rings. When symmetrical, the compounds are generally solid compounds. Liquid compounds are formed when a sufficient number of the R groups are substituted so as to form liquid triaryl thiophosphate mixtures. The aryl rings are preferably unmodified but may have other modifying groups (other than those of the liquid compositions) such as Cl, $NO_2$, CN, and Br. Illustrative of these compounds is triphenyl thiophosphate, diphenyl mono-p-xenyl thiophosphate, di-o-chlorophenyl mono-p-tertiarybutylphenyl thiophosphate and the like. These compounds can be prepared by reacting a mixture of unsubstituted and substituted hydroxyaryl compounds with a phosphite in the form of the halide followed by sulfurization or with thiophosphoryl halide without sulfurization. Representative hydroxyaryl compounds include phenol, cresol, mixed cresols, ethylphenol, isopropylphenol, chlorophenol, nitrophenol, 2,4-dibromophenol, 2,3,6-trichlorophenol, octylphenol, diethylphenol, hexylphenol, cyclohexylphenol, isopropylmeta-cresol, isopropyl-ortho-cresol, orthoxenol, naphthol, p-tertiaryoctylphenol, 3,5-diethylphenol and the like. The substituents can be in the ortho, meta and/or para position on the aromatic ring. Preferably the R group is phenyl or substituted phenyl. The invention will be discussed in connection with the preferred embodiment phenol though the discussion applies equally to other phenols and aromatic compounds.

The compositions of the invention can be prepared by forming a mixture of phenol and substituted phenol. This can be accomplished by mixing the phenol with the substituted phenol. Preferably, the mixture is prepared in situ by reacting phenol with an alkylating agent having from $C_2$ to $C_8$ carbon atoms. Alkylating agents such as isobutylene and propylene are preferred. The conditions of reaction are well known to one of ordinary skill in the art. The alkylating agent is used in an amount sufficient to provide a molecular weight ratio of alkylating agent/phenol of within the range of from about 0.2 to about 0.8 and preferably from about 0.3 to about 0.6 to provide a molecular weight ratio of substituted phenol/phenol within the range of from about 0.25 to about 4.0.

The mixture of phenol and substituted phenol is then reacted with a phosphorus trihalide, e.g., chloride or bromide, in an amount sufficient to completely substitute the halide cites though more or less can be used. Generally 3.3 molecular equivalents (a 10% excess) of the phenols per molecular equivalent of phosphorus trihalide is used. The reaction is carried out by heating a mixture of reactants to a temperature at which hydrogen halide is evolved, i.e. between about 30° C. and about 200° C. If desired, a nitrogen sparge and a catalyst such as a metal or metallic chloride catalyst can be employed. Any excess phenol can be stripped under vacuum. The triaryl phosphite/mixed triaryl phosphite product can then be reacted directly with sulfur to form the triaryl thiophosphate/mixed triaryl thiophosphate final product. The reaction with the sulfur is generally carried out by heating the reactants with an amount of sulfur, preferably powdered sulfur, equimolar to the phosphite at temperatures ranging from about 140° C. to about 250° C. for a sufficient time to accomplish the reaction depending on temperature and reactants, e.g., for about 1–3 hours.

In order to obtain a colorless, odorless stable product, the product must be washed with an aqueous base solution and, following separation, dried under mild conditions. Any aqueous alkaline solution can be used, preferably alkali and alkaline earth metal oxides and hydroxides. Alkalinity within the range of from about pH 10 to about pH 13 is preferred.

If the product is viscous, it may be desirable to thin the product with an organic water-immiscible solvent which is inert to the product. To avoid separation conditions requiring temperatures which can cause product decomposition, solvents with low boiling points are preferred. Solvents which are preferably used have boiling points below about 120° C. These solvents can be illustrated by mixed hexanes, cycloalkanes such as cyclohexane, mixed ketones, and toluene. While fractional distillation can be used to purify the final product, this is less desirable as the product tends to decompose to a small degree during distillation leading to odors and often colors in the final product.

The product, optionally thinned for washing, is washed with an aqueous base solution to separate impurities. Multiple washing may be desirable. The amount of wash solution used is that needed to effect the washing. Equal volumes have been found to be effective. The product is then water washed, preferably until the pH of the product is within the range of from about 6.5 to about 7.5.

After separation of the organic product fraction from the aqueous fraction, the organic product is dried under conditions sufficiently mild to avoid a significant degree of decomposition of the product fraction such as by azeotorpic solvent stripping or by using desiccants, e.g., toluene or anhydrous magnesium sulfate. "Significant degree of decomposition" is intended to mean a level of decomposition sufficient to provide a discernible disagreeable odor. Any thinning solvent can be removed by mild distillation. While the product may be purified by distillation, it is essential in the practice of the invention that the product be base washed and mild dried after any distillation which causes significant product decomposition. Solvent stripping must be accomplished under mild conditions to avoid product decomposition. In the preferred form of the invention, the product is not fractionally distilled thus avoiding thermal decomposition resulting in odor in the product. A colorless, odorless stable product is obtained.

The compositions of the present invention comprise a mixture of symmetrical triaryl thiophosphates which are normally solid in pure form, and mixed triaryl thiophosphates in liquid form. A sufficient quantity of the mixed triaryl thiophosphate is present to form a liquid mixture. Preferably, the liquid mixed triaryl thiophosphates comprise a blend of at least 25 percent symmetrical triaryl thiophosphate and a sufficient amount of liquid substituted triaryl thiophosphate to form a liquid mixture. More preferably, the composition comprises at least 30 percent diphenyl t-butylphenyl thiophosphate and at least 40% symmetrical triaryl thiophosphate.

The compounds of the invention can also be prepared by reacting thiophosphoryl chloride with the phenol/mixed phenol blend. The sulfurization step can be avoided though the other steps apply. When using thiophosphoryl chloride it is again important to the operation of the invention that any distillation be prior to the base washing and mild drying.

The compositions of the present invention can be used as effective flame retardants in polymers such as the polyphenylene ethers and blends with other polymers as described in U.S. Pat. Nos. 3,306,874 and 3,306,875 of Allan S. Hay and U.S. Pat. Nos. 3,257,357 and 3,257,358 as well as 3,383,435 (blend with polystyrene) and 3,361,851 (blend with polyolefins). The flame retardants of the invention are compatible with polyphenylene ether polymers and additives normally used in connection therewith such as the stabilizers disclosed in U.S. Pat. No. 4,255,321. The compositions of the present invention are liquid throughout a wide temfperature range and can be easily admixed with the polymers. Further, the melting point can be depressed to such a degree that cold temperatures of the blend which might occur during shipping will not affect the blend.

The present invention is more fully illustrated in the following examples.

EXAMPLE 1

A mixture of tert-butyl phenol and phenol prepared by alkylating phenol with isobutylene to a $C_4$/phenol ratio of 0.25 to provide a t-butyl phenol/phenol mixture was flash distilled to remove color. The mixture had an average t-butyl:phenyl ratio of about 0.3 (about 25% phenol:75% t-butyl phenols). 360.7 grams of t-butyl phenols/phenol mixture was heated to 70°–75° C. under a nitrogen atmosphere and 137.3 grams (1.0 mole) of $PCl_3$ was added dropwise at such a rate that excess reflux of $PCl_3$ (b.p. 76° C.) did not occur. After completion of addition, the temperature was gradually elevated to 150° C. and held at that temperature for 1 hour after the reaction was completed. The heated reaction mixture was sparged with dry nitrogen to drive off any residual hydrogen chloride. Unreacted phenols were removed by distillation (about 32 grams). 319 grams of a phosphite mixture containing triphenyl and various t-butylphenyl/phenyl phosphites was obtained.

300 grams (0.843 mole) of the phosphite mixture containing triphenyl phosphite and various phenyl t-butylphenyl phosphites was placed in a 500-milliliter, 3-neck round bottom flaks and heated under nitrogen atmosphere to 150° C. Flowers of sulfur (27 grams, 0.843 moles) was added in portions and the temperature was held at 150° C. for ½ hour. After the addition had been completed, the temperature was raised to 180° C. and was held at that temperature for 2 hours.

The product (about 325 grams) was transferred to a separatory funnel and thinned with 150 grams hexane for washing with three 108 gram aliquots of 5% sodium hydroxide and with four 108 gram aliquots of water to a pH of not more than 7. The product was dried over magnesium sulfate and the hexane was then stripped on a rotary evaporator. The recovered weight was 309.2 grams of product (94.5% yield). The final product was a colorless liquid without an odor at room temperature.

Gas chromatographic analysis revealed 44 area percent of triphenyl thiophosphate, 40% diphenyl t-butylphenyl thiophosphate. 14% of mixed phenyl t-butylphenyl thiophosphates, 1% triphenylphosphite and 0.3% triphenylphosphate. $P^{31}$NMR analysis revealed 96 mole percent for six thiophosphate isomers, 2.5% for triphenyl phosphite, and 0.8% for triphenyl phosphate.

EXAMPLE 2

2,465 grams of a phosphite mixture containing triphenyl phosphite and various phenyl t-butylphenyl phosphites prepared in accordance with the procedure of Example 1 was placed in a 5 liter, 3-neck flask equipped with mechanical stirrer, reflux condenser, Claisen adapter, thermometer, nitrogen inlet and outlet bubblers, and solids addition funnel. The ratio of t-butyl to phenyl was about 0.3. The mixture was heated, under nitrogen, to 150° C.

To the heated mixture was incrementally added 227.4 grams (7.1 moles) of flowers of sulfur (2.5% excess). After addition of the sulfur had been completed, the resulting composition was heated for ½ at 150° C. The temperature was then raised to 180° C. and held at that temperature for 2 additional hours. Hexane (1.41 liters) was then added to thin the mixture for washing with 3 aliquots (897.5 grams) of 5% NaOH and 2 aliquots (897.5 grams) of water at room temperature. The pH after washing was 7.0. The hexane was stripped off using a rotary evaporator. The recovered weight of thiophosphate product was 2633.2 grams (97.8% yield). To this product was added FILTER-CEL filter aid and the mixture was filtered through a FILTER-CEL filter bed.

Gas chromatographic analysis indicated a trace quantity (0.453 area percent) of hexane still present in the product. The thiophosphate mixture was charged to a 3 liter 1-neck flask with a thermometer well, gas dispersion tube, gas drier, thermometer, gas inlet tube and vacuum sideline adapter, magnetic stirrer bar, vacuum regulator, and 3 liter heating mantle. The thiophosphate mixture was sparged for 2.5 hours at 45° C. under vacuum. Samples were taken from time to time and injected neat into the gas chromatographic analyzer. After 2.5 hours no peak indicating hexane solvent was recorded. The material was filtered twice. The APHA color for the material was about 20.

Gas chromatographic analysis of the resulting product detected no phenols. $P^{31}$NMR showed 96 mole percent thiophosphate isomers, 3.56% triphenyl phosphite and 0.5% triphenyl phosphate.

EXAMPLE 3

A phosphite mixture containing triphenyl phosphite and various phenyl t-butylphenyl phosphites (331.7 grams) prepared using the general method as outlined in Example 1 was placed in a 3-neck 1 liter flask. To this mixture was added 29.0 grams (0.9 moles) of flowers of sulfur. The addition of the sulfur took place incrementally at 150° C. followed by ½ hour heating at 150° C. with 2 hours heating at 180° C. 200 grams of hexane was added to the product to thin it for washing. The resulting thinned thiophosphate product was washed with 3 aliquots (135 grams) of 5% sodium hydroxide solution and 2 aliquots of 135 grams each of water. The pH of the product was 7. The hexane was stripped off with a rotary evaporator. Toluene was added and the product was redissolved in order to azeotrope off any remaining water. The toluene was removed on a rotary evaporator yielding a product that weighed 341.5 grams. To the product was then added FILTER-CEL filter medium with stirring. The material was the filtered through a FILTER-CEL bed on a Buchner funnel while warm. Some residual cloudiness in the material disappeared. The yield of product was 94.7% of theoretical.

Qualitative gas chromatography of the product (8633.17) revealed:

Three major peaks (18–42%), five minor peaks (1–3%) and six low level peaks (0.1–0.3%) all in the range expected for triaryl and t-butylated triaryl thio phosphates. The tert-butylated phenol used to prepare the phosphate had the following analysis:

| Area % phenol — | 67.29 |
|---|---|
| Area % o-TBP — | 0.91 |
| Area % p-TBP — | 36.47 |
| Area % 2,6 di-TBP — | 0.33 |
| $C_4$/phenyl ratio = | 0.276 |

What is claimed is:

1. A process for preparing liquid mixed triaryl thiophosphates which comprises reacting a phosphorus halide or a thiophosphoryl halide with a blend of hydroxy aryl compounds and substituted derivatives thereof wherein the quantity of substituted derivatives is sufficient to liquify a normally solid triaryl thiophosphite, and, in the case of phosphorus halide, sulfurizing the phosphite to form the thiophosphate, washing the thiophosphate with aqueous base to remove impurities and drying the so washed thiophosphate under conditions sufficiently mild to avoid any significant degree of decomposition of the thiophosphate.

2. The process according to claim 1 wherein said hydroxy aryl compound is phenol.

3. The process according to claim 1 where the substituent on substituted derivative is a $C_2$ to $C_8$ aliphatic radical.

4. The process as recited in claim 3 wherein the ratio of aliphatic radicals to aryl compounds ranges from about 0.2 to about 0.8.

5. The process according to claim 4 wherein said ratio ranges from about 0.3 to about 0.6.

6. The process according to claim 1 wherein the viscosity of the thiophosphate is reduced prior to washing by admixing therewith an amount of an inert water-immiscible organic solvent sufficient to thin the product to a viscosity sufficient to facilitate washing.

7. The process according to claim 6 wherein said solvent has a boiling point below about 120° C.

8. The process according to claim 3 wherein said radical is propyl or butyl.

9. The process according to claim 3 wherein said radical is isopropyl or tert-butyl.

10. A liquid mixed triaryl thiophosphate comprising a blend of at least 25 percent symmetrical triaryl thiophosphate, and, substituted triaryl thiophosphates in an amount sufficient when combined with the symmetrical triaryl thiophosphate to form a liquid mixed triaryl thiophosphate composition.

11. The composition as recited in claim 10 wherein the substituent on said substituted triaryl thiophosphates is a $C_2$ to $C_8$ aliphatic radical.

12. The composition according to claim 11 wherein said radical is propyl or butyl.

13. The composition according to claim 11 wherein said radical is isopropyl or tert-butyl.

14. The composition according to claim 13 wherein said radical is a tertiary butyl radical.

15. The composition as recited in claim 10 which comprises at least 25 percent diphenyl t-butylphenyl thiophosphate and at least 40 percent triphenyl thiophosphate, said percentages being by weight based on the weight of the two claimed compounds.

16. The product of the process of claim 1 wherein said product is a blend of at least 25% symmetrical triaryl thiophosphate, and, substituted triaryl thiophosphates in an amount sufficient when combined with the symmetrical triaryl thiophosphate to form a liquid mixed triaryl thiophosphate composition.

* * * * *